United States Patent [19]

Granzow et al.

[11] Patent Number: 4,560,472

[45] Date of Patent: Dec. 24, 1985

[54] PERITONEAL DIALYSIS APPARATUS

[75] Inventors: Daniel B. Granzow, Ingleside; Arthur L. Lueders, Mundelein, both of Ill.; Ralph L. Davis, Burlington, Wis.; Stanley J. Pernic, Round Lake, Ill.; James R. Hitchcock, Jr.; Francis D. Buckley, both of Barrington, Ill.

[73] Assignee: Baxter Travenol Laboratories, Inc., Deerfield, Ill.

[21] Appl. No.: 448,450

[22] Filed: Dec. 10, 1982

[51] Int. Cl.$^4$ .............................................. B01D 31/00
[52] U.S. Cl. .................................... 210/140; 210/927; 604/29
[58] Field of Search ................... 604/28, 29; 210/927, 210/321.1, 195.2, 140, 441

[56] References Cited

U.S. PATENT DOCUMENTS

| 3,185,153 | 5/1965 | Leucci | 128/227 |
|---|---|---|---|
| 3,410,268 | 11/1968 | Leucci | 128/227 |
| 3,709,222 | 1/1973 | DeVries | 128/213 |
| 3,730,183 | 5/1973 | Goldsmith et al. | 128/213 |
| 3,783,866 | 1/1974 | Tirkkonen | 128/213 |
| 3,872,863 | 3/1975 | Lasker et al. | 128/213 |
| 4,085,046 | 4/1978 | Saporito, Jr. | 210/90 |
| 4,096,859 | 6/1978 | Agarwal et al. | 128/213 |
| 4,240,408 | 12/1980 | Schael | 128/1 R |
| 4,252,115 | 2/1981 | Schael | 128/213 A |
| 4,275,726 | 6/1981 | Schael | 128/213 A |
| 4,282,902 | 8/1981 | Haynes | 137/636.1 |
| 4,381,003 | 4/1983 | Buoncristiani | 128/213 A |

FOREIGN PATENT DOCUMENTS

| 2809303 | 10/1978 | Fed. Rep. of Germany | 604/29 |
|---|---|---|---|
| 642748 | 9/1950 | United Kingdom | 210/411 |

Primary Examiner—Frank Spear
Attorney, Agent, or Firm—Paul C. Flattery; Daniel D. Ryan; Thomas A. Kmiotek

[57] ABSTRACT

An automatic cycler for performing Continuous Cycling Peritoneal Dialysis (CCPD) and Intermittent Peritoneal Dialysis (IPD) is provided. The apparatus of the present invention is a safe and convenient cycler apparatus for performing peritoneal dialysis in either home or clinical environment. The apparatus provides a stable base by storing dialysate at a relatively low position. Tubing administration set length is reduced to a minimum by the use of individual, separated valves and by the elimination of redundant, duplicate tube sections. Administration set complexity is reduced by the use of a conventional design dialysate container for heating and weighing of an infusing dialysate dosage. The apparatus allows for gravity feed to a patient with an optional capability of adjusting the pressure head for the gravity feed.

12 Claims, 7 Drawing Figures

FIG. 2

| VALVE MEANS | VALVES | VALVE POSITION | PUMP FUNCTIONING |
|---|---|---|---|
| FIRST | 36 & 40 | X = CLOSE | + = NOT RUNNING |
| SECOND | 40 & 42 | O = OPEN | [ ] = RUNNING |
| THIRD | 42 & 44 | | |
| FOURTH | 40 & 44 | | |
| FIFTH | 38 & 40 | | |

| CYCLE | PHASE | VALVE | | | | | PUMP |
|---|---|---|---|---|---|---|---|
| | | 42 | 40 | 44 | 36 | 38 | 20 |
| | INITIAL HEATING OF DIALYSATE | X | X | X | X | X | + |
| I | DRAIN PATIENT | O | X | O | X | X | + |
| I | FILL PATIENT | O | O | X | X | X | + |
| I | DWELL | X | X | X | X | X | + |
| I | REFILL HEATER AND WEIGH STATION | X | O | X | O | X | [ ] |
| I | HEAT DIALYSATE | X | X | X | X | X | + |
| II | DRAIN PATIENT | O | X | O | X | X | + |
| II | FILL PATIENT | O | O | X | X | X | + |
| II | DWELL | X | X | X | X | X | + |
| II | REFILL HEATER AND WEIGH STATION | X | O | X | O | X | [ ] |
| II | HEAT DIALYSATE | X | X | X | X | X | + |
| III | DRAIN PATIENT | O | X | O | X | X | + |
| III | FILL PATIENT | O | O | X | X | X | + |
| III | DWELL | X | X | X | X | X | + |
| IV | DRAIN HEATER AND WEIGH STATION | X | O | O | X | X | + |
| IV | REFILL HEATER AND WEIGH STATION | X | O | X | X | O | [ ] |
| IV | HEAT DIALYSATE | X | X | X | X | X | + |
| V | DRAIN PATIENT | O | X | O | X | X | + |
| V | FILL PATIENT | O | O | X | X | X | + |

PERITONEAL DIALYSIS APPARATUS

FIELD OF THE INVENTION

This invention relates to an apparatus used in performing peritoneal dialysis therapy. The invention particularly relates to an apparatus that is useful as an automatic cycler for performing peritoneal dialysis, specifically, Continuous Cycling Peritoneal Dialysis (CCPD) and Intermittent Peritoneal Dialysis (IPD).

BACKGROUND OF THE INVENTION

Currently, the most widely used method of kidney dialysis for treatment of end stage renal disease is hemodialysis. In hemodialysis, the patient's blood is cleansed by passing it through an artificial kidney in an artificial kidney dialysis machine. During dialysis, venous and arterial blood lines convey a patient's blood to and from the artificial kidney. Impurities and toxins are removed from the patient's blood by diffusion across a semipermeable membrane in the artificial kidney. Hemodialysis is generally required three times a week with each dialysis requiring four to five hours in a dialysis center or at home.

Peritoneal dialysis, although used less frequently than hemodialysis, is an accepted method for treating end stage renal disease. It is becoming increasingly a more popular form of dialysis. In peritoneal dialysis, a dialysis solution—also referred to as dialysate—is infused into a patient's peritoneal cavity using tubing and a catheter. The peritoneum, which defines the peritoneal cavity, contains many small blood vessels and capillary beds which act as a natural, semipermeable membrane. This natural membrane may be contrasted with the artificial membrane used in hemodialysis. Nonetheless in both cases, impurities and toxins in the blood are removed by diffusion across a membrane.

In peritoneal dialysis, dialysis solution remains in the patient's peritoneal cavity for a time sufficient for blood impurities to be removed by diffusion across the peritoneal membrane and into the dialysis solution. The impurity-containing or spent dialysis solution then is drained from the peritoneal cavity, typically by means of the infusing catheter and tubing. A fresh supply of dialysis solution replaces the spent, impurity-containing, drained solution.

Dialysis therapy includes two forms of peritoneal dialysis treatment pertinent to the present invention. Continuous Cycling Peritoneal Dialysis (CCPD) uses auxiliary apparatus to cycle dialysis solution through a patient's peritoneal cavity, typically during the sleeping hours. A patient generally undergoes dialysis treatment each night. Intermittent Peritoneal Dialysis (IPD) similarly uses auxiliary apparatus to infuse dialysis solution into the peritoneal cavity and drain dialysis solution from a patient's peritoneal cavity at a rate much faster than in CCPD. Similar to hemodialysis, and unlike CCPD, IPD therapy is conducted intermittently during the week, typically in four to five hour sessions, three times a week. The volumes of dialysis solution are rapidly infused and drained to accomplish the dialysis within this time period. In CCPD and IPD, infusion and draining of dialysate are accomplished using tubing and a surgically implanted, indwelling catheter in communication with the patient's peritoneal cavity.

It would be desirable to provide a safe, automatic apparatus for performing peritoneal dialysis. Such an apparatus would be suitably automatic and convenient so that it can be used by the home patient or by staff in a hospital or clinic. The peritoneal dialysis apparatus would have the capability of performing both CCPD therapy and IPD therapy—in home and hospital environments—with only minor adjustments to the apparatus and without increasing the complexity of a basic apparatus design.

For CCPD, it would be advantageous to provide an apparatus which would selectively infuse different formulations of dialysis solution which are adapted to account for different periods of dwell inside the patient. The last dosage of dialysate administered to CCPD therapy patients dwells in the peritoneal cavity until the next dialysis procedure. This time period could be as long as 16 hours. It would be desirable for the apparatus to infuse a first formulation of dialysis solution during the initial cycles of a dialysis treatment yet having the capability of infusing a second formulation for the last dosage of dialysate administered, that is, a "final fill". The second formulation of dialysate would be chosen especially because of a longer dwell period in the patient.

It would be expedient to provide an apparatus with a stable base. Usually, all but an infusing dosage of dialysate would be stored at a relatively low level. A fixed column, preferably supporting approximately a single infusion dialysate dosage, would be higher than the stored dialysate to provide gravity feed of the infusion dialysate to the patient. Alternatively, the support column would be adjustable to allow control of the head pressure of the infused dialysate.

In some situations, more than a single infusion dialysate dosage would be supported at the support column. For example, in pediatrics, the infusion dialysate in a conventional design container could contain several dosages. Generally, though, total volume of infusion dialysate supported at the column would be less than the volume stored at a relatively low level. This would promote a more stable design.

It would be expedient to reduce the length of the tubing set which carries dialysate from storage to heater to patient and to drain. Apparatus having valves banded together, or ganged, require longer tubing sets since all tubing must be routed to the ganged valves from the isolated stations of the apparatus and back if fluid flow therein is to be regulated by the valves of the apparatus. It would be desirable to provide separated valves which would be appropriately placed for regulating dialysate flow in a tube rather than extending the length of the tube to communicate with the valve.

Tubing set length also can be reduced by using common tube sections for the different dialysate flow paths to and from the separate stations of the apparatus. An apparatus having simultaneous fluid flow between different stations of the apparatus requires duplicate portions of tube sections. It would be advantageous to eliminate this redundancy by providing an apparatus which sequentially controls fluid flow between different stations of the apparatus as opposed to simultaneous flow.

It would be desirable to reduce the complexity and cost of a tubing set by eliminating the need for a specially designed container to hold dialysate for heating and weighing prior to infusion into a patient. An elegant design would be capable of accepting a conventional dialysate container bag at the heater and weigh station thereby eliminating the need for a specially designed container.

BRIEF SUMMARY OF THE INVENTION

The present invention provides a safe and easy-to-operate automatic apparatus for performing peritoneal dialysis. The apparatus may be used conveniently by a patient in the home or by trained staff in hospitals or dialysis centers. The apparatus is a compact and stable design. It can withstand slight pushing forces without tipping over. Roller wheels on the apparatus enable the machine to be moved easily from room to room by a patient or a technician. The apparatus has the capability of performing CCPD and IPD therapy with only minor adjustments to the apparatus and without a design of increased complexity.

The apparatus of the present invention comprises a dialysate supply station. Bags or containers of dialysis solution are conveniently arranged at this station for storage. Typically, in preferred applications, approximately a single dosage of dialysate is contained at a heater and weigh station in a conventional design container. The dialysate supply station is designed to accommodate enough containers of a first formulation of dialysis solution for performing a complete CCPD procedure or a complete IPD procedure depending on the particular therapy chosen.

The dialysate supply station optionally includes a separate, additional container containing a second formulation of dialysis solution for the last infused dosage or final fill in CCPD. Final fill solution is chosen especially because it will dwell in the peritoneal cavity between therapies and for a longer period of time. In CCPD this time period may be as long as 16 hours.

The dialysis solution containers at the dialysate supply station preferably are located approximately waist high and typically at the same height as the basic apparatus hardware. This design provides a stable base for the apparatus since, preferably, all but an infusing dosage of dialysate is stored at a relatively low level. A column supports the heater and weigh station. In a preferred application the heater and weigh station contains approximately a single infusion dialysate dosage. For a gravity feed to the patient, the infusion dialysate is located higher than the dialysate stored at the dialysate supply station.

The heater and weigh station heats dialysis solution to approximately body temperature and weighs the correct dosage for infusion. The column supporting the heater and weigh station and the infusion dialysate may be adjustable to allow control of the head pressure for infused dialysate. Solution delivery means of this apparatus can comprise tubing and connection devices for attachment to a catheter implanted in a patient's peritoneal cavity. This apparatus also includes a drain and weigh station for monitoring spent dialysis solution.

Flow paths connect the different stations and means of the present invention. A first fluid flow path connects the dialysate supply station and the heater and weigh station. A second fluid flow path connects the heater and weigh station and the solution delivery means. The solution delivery means and the drain and weigh station are connected by a third fluid flow path. Connecting the heater and weigh station and the drain and weigh station is a fourth fluid flow path.

The apparatus of the present invention also includes pump means for pumping dialysate. Valve means are provided for controlling dialysate flow in the first, second, third and fourth fluid flow paths. Control means in the apparatus dictates the sequence of valve openings. The control means also controls the time intervals during which different valves and flow paths are open and when the pump means is pumping.

In operation, the dialysate supply station comprises containers of a first formulation of dialysis solution which are used in performing peritoneal dialysis. A container of a second formulation of dialysis solution for the last infusion or final fill also may be provided. Another container of the first formulation of dialysis solution may be provided at the heater and weigh station. At least one large drain container may be provided at the drain and weigh station. A disposable tubing set interconnects the containers of dialysis solution and the other stations and means in the apparatus.

Tubing connecting the standard dialysis solution container in the dialysate supply station and the heater and weigh station constitutes the first fluid flow path. The first fluid flow path passes through a pump for pumping dialysis solution from the supply station to the heater and weigh station. First valve means controls the dialysate flow through the tubing. The proper dosage for infusion is weighed at the heater and weigh station and heated for a time sufficient to raise the temperature of the dialysis solution to approximately body temperature. Optionally, when a final fill dialysate container for CCPD is included in the dialysate supply station, tubing connecting the final fill container and the heater and weigh means constitutes the fifth fluid flow path. Fifth valve means controls the flow of dialysate in the fifth fluid flow path.

Heated dialysate flows from the heater and weigh station to the solution delivery means (typically a catheter connection attached to an implanted catheter) through a second fluid flow path connecting the two. Second valve means controls dialysate flow in the second fluid flow path. A third fluid flow path connects the solution delivery means to a drain and weigh station. Third valve means controls dialysate flow in the third fluid flow path. After the dialysis solution has dwelled inside the patient for a prescribed period of time, the third valve means is opened and spent dialysate can drain under the force of gravity to the drain and weigh station. The amount of dialysate exiting the patient is determined by weight differential at the drain and weigh station.

A tubing set defines the flow paths. The first fluid flow path and the second fluid flow path use a common tube section in the tubing set. Similarly, the second and third fluid flow paths use common tube sections. The fourth fluid flow path has tube sections in common with the other fluid flow paths. And, the fifth fluid flow path has tube sections in common with the first and second fluid flow paths. Redundant, duplicate tube sections are eliminated. Dialysate flow in the flow paths is sequential rather than simultaneous.

The valve means in the present invention are comprised of decentralized, individual valves. Elegant placement of separate, individual valves at critical positions on the apparatus obviates routing of tubes from the isolated stations in the apparatus to the valves and then back. The different valve means, however, have individual valves in common. The first and second; second and third; first and fourth; second and fourth; first and fifth; second and fifth; third and fourth; and fourth and fifth valve means have common valves.

Control means in the apparatus of the present invention dictates the time intervals and sequence during which valve means and flow paths are opened and closed. Proper phases in the cycling of dialysis solution are controlled by the sequence of the opening and closing of the valves constituting the valve means in the apparatus. Controlled and monitored flows are between the dialysate supply station and the heater and weigh station, between the heater and weigh station and the solution delivery means, between the solution delivery means and the drain and weigh station, and between the heater and weigh station and the drain and weigh station.

An initial drain phase begins the cycling. The third valve means is opened which allows fluid to flow from the solution delivery means to the drain and weigh station (third fluid flow path). The control means maintains the third fluid flow path open for a prescribed drain time. At the end of this drain time, the apparatus automatically initiates the first patient fill phase of the cycle. A typical CCPD procedure involves four patient drain and fill phases.

The third valve means is closed when the patient fill phase of the cycle begins, thus stopping fluid flow in the third fluid flow path. The second valve means is opened allowing heated dialysate to flow between the heater and weigh station and the solution delivery means (second fluid flow path) for the patient fill phase of the cycle. Fill time is measured and the weight amount of dialysate is monitored by the control means. After successful filling of the patient, the second valve means is closed. Fluid flow ceases in the second fluid flow path.

After the patient fill phase has been completed, the third valve means remains closed preventing dialysate flow between the solution delivery means and the drain and weigh station. The dwell phase of the CCPD or IPD cycle then begins. Dialysate dwells in the patient's peritoneal cavity for a prescribed period of time programmed into the control means. Dialysate flow between the dialysate supply station and the heater and weigh station occurs during the patient dwell phase. First valve means is opened and the pump means pumps dialysate from the dialysate supply station to the heater and weigh station (first fluid flow path). Once the prescribed quantity of dialysate is at the heater and weigh station, the pump means stops pumping. Fresh dialysate residing in the heater and weigh station is heated to approximately average body temperature.

The patient drain phase of the next cycle begins once the dwell phase has been completed. Third valve means opens allowing dialysate flow in the third fluid flow path. The first and second valve means remain closed at this time, preventing dialysate flow between the dialysate supply station and the heater and weigh station (first fluid flow path) and between the heater and weigh station and the solution delivery means (second fluid flow path). The patient drains for the prescribed drain time while the weight amount of dialysate drained is monitored by the control means.

The apparatus of the present invention is a safe and convenient cycler apparatus for performing peritoneal dialysis. The apparatus of the present invention has the capabilities of measuring precise dosage to the patient rather than relying on time and flow rate measurements. Heretofore unachieved benefits are realized by the present design.

A benefit of the apparatus of the present invention is the ability to selectively infuse different formulations of dialysis solution which are adapted to account for different periods of dwell inside the patient. A first formulation of dialysis solution may be infused during the initial cycles of a dialysis procedure. In CCPD a second, final fill formulation of dialysis solution may be infused as the last dosage of the therapy. The last dosage of dialysate administered in CCPD will dwell in the peritoneal cavity of a patient until the next dialysis procedure. The second formulation would be chosen especially because of the long dwell period between treatments.

A stable base is another benefit of this apparatus design. In most treatment situations, all but an infusing dosage of dialysate may be stored at a relatively low level.

The patient benefits from gravity feed of dialysate from infusion dialysate contained at a support column located above the stored dialysate.

Also benefiting the patient is optional adjustability of the support column which allows control of the infused dialysate pressure head.

A considerable achievement of the present invention is the reduced tubing set length. The use of separated, individual valves allows their strategic placement. This obviates routing of tubes from isolated stations in the apparatus to the valves and then back. Set size is reduced to a minimum when compared to peritoneal dialysis apparatus having ganged valves.

Total tubing set length and hence, cost of a disposable set are reduced to a minimum by eliminating redundant, duplicate portions of the tube section. This benefit is achieved by using common tube sections for fluid flow paths to the stations of the apparatus.

Additional benefits achieved by this invention are realized in the combined heater and weigh station structure which is located on the adjustable support column. Heating and weighing functions are combined in one unit.

By this design, a conventional design dialysate container bag is used at the heater and weigh station. A specially designed heater bag which normally might be provided with the tubing administration set is no longer needed. Essentially, the conventional design container bag carried at the heater and weigh station in the invention of this application is a dual function bag; first, as a conventional dialysate container for containing the dialysate and second, as a heater and weigh container for containing heated and weighed dialysate prior to infusion into a patient. As a consequence, tubing set complexity and cost are further reduced by eliminating an extra, specially designed heater bag.

Other benefits and advantages of this invention will become apparent upon reading the following detailed description and appended claims.

BRIEF DESCRIPTION OF THE DRAWINGS

For a more complete understanding of this invention reference should now be had to the embodiments illustrated in greater detail in the accompanying drawings.

In the drawings:

FIG. 2 portrays the sequence of operation of the valves in a preferred peritoneal dialysis apparatus of this invention for a complete CCPD treatment.

FIG. 6 is a perspective view of a portion of the apparatus shown in FIG. 4 used for weighing spent dialysis fluid.

DESCRIPTION OF THE PREFERRED EMBODIMENTS

Figure 1:
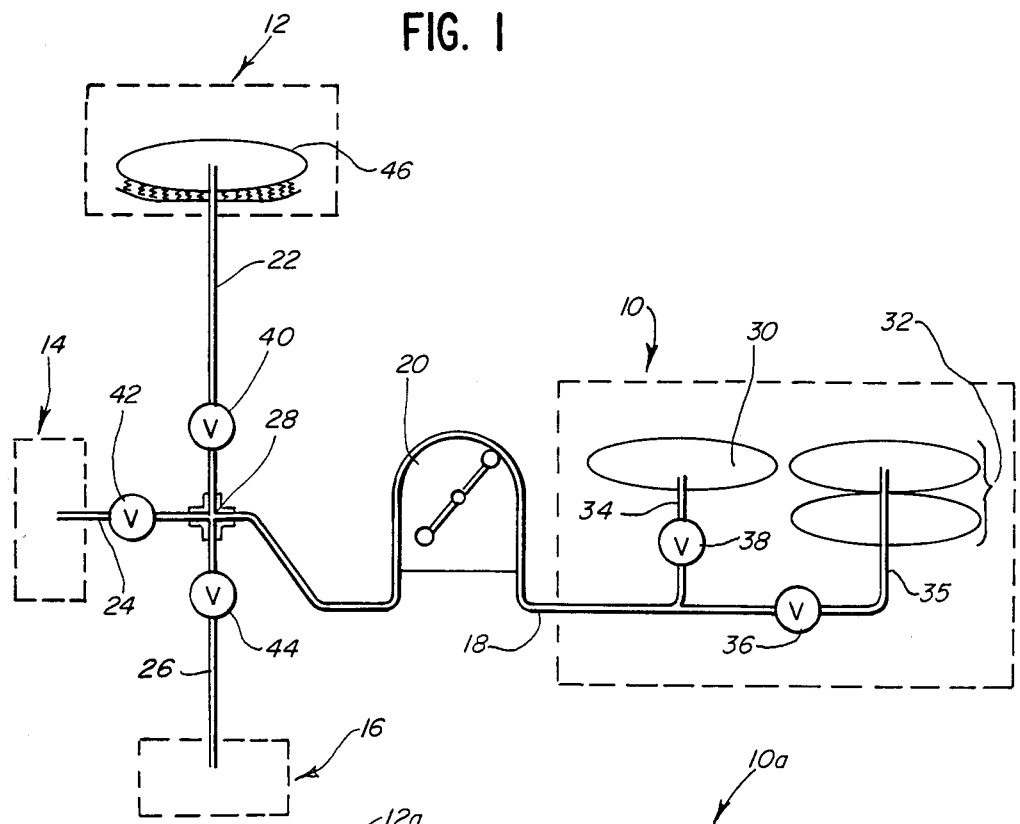
FIG. 1 is a schematic diagram showing the basic components of a peritoneal dialysis apparatus of this invention used in performing a CCPD treatment.

Turning now to the drawings, FIG. 1 is a schematic representation of the basic elements in the peritoneal dialysis apparatus of the present invention. The apparatus has dialysate supply station 10, heater and weigh station 12, solution delivery means 14 and drain and weigh station 16. Fluid flow paths communicate with the various stations and means. Conduit 18 communicates with dialysate supply station 10 and passes through pump means 20, which may be a peristaltic roller pump. Conduit 22 communicates with heater and weigh station 12. Conduit 24 communicates with solution delivery means 14; and conduit 26 communicates with drain and weigh station 16. Conduits 18, 22, 24 and 26 are joined together at "X" connector 28.

In the embodiment illustrated in FIG. 1, dialysate supply station 10 comprises final fill dialysate container 30 and standard dialysate containers 32. The designations "final fill" and "standard" dialysate containers merely indicate that different dialysate formulations are contained therein. "Standard" refers to formulations used in initial cycling phases. "Final fill" refers to the last dosage of dialysate infused (in CCPD) which resides in the patient between therapies, generally throughout the daytime hours.

Conduit 34 connects final fill dialysate container 30 to conduit 18. Conduit 35 connects standard dialysate containers 32 to conduit 18. Final fill dialysate container 30, conduit 34, and valve 38 optionally are part of dialysate supply station 10.

Different valve means in the present invention are comprised of combinations of individual valves. Individual valves are located along the conduits of the apparatus. Valve 36 is located between conduits 18 and 35 and valve 38 is located between conduits 18 and 34. Valves 40, 42 and 44 regulate fluid flow in conduits 22, 24 and 26.

Conduits 35, 18 and 22 define the first fluid flow path connecting dialysate supply station 10 and heater and weigh station 12. A second fluid flow path connecting heater and weigh station 12 and solution delivery means 14 is comprised of conduits 22 and 24. Conduits 24 and 26 constitute a third fluid flow path connecting solution delivery means 14 and drain and weigh station 16. In addition to these three fluid flow paths, an embodiment of the apparatus can optionally have fourth fluid flow path comprising conduits 22 and 26. Also, when dialysate supply station 10 additionally comprises final fill dialysate container 30, conduit 34, and valve 38, a fifth fluid flow path is comprised of conduits 34, 18 and 22.

Valves 36 and 40 constitute first valve means which open to permit dialysate flow through the first fluid flow path. Second valve means include valves 40 and 42 which can open to permit dialysate flow in the second fluid flow path. Dialysate flow in the third fluid flow path is controlled by third valve means including open valves 42 and 44. When the apparatus of the present invention additionally comprises the fourth fluid flow path and the fifth fluid flow path, fourth and fifth valve means are provided. Fourth valve means comprises open valves 40 and 44. Fifth valve means comprises open valves 38 and 40. Dialysate flow in first through fifth fluid flow paths follows a prescribed sequence during cycling. Flow of dialysate in these paths is not simultaneous.

Control means in the peritoneal dialysis apparatus of the present invention dictate the sequencing and time intervals during which particular valve means are open or closed and during which the pump means is pumping. It should be realized that the valve means in this embodiment of the present invention are comprised of more than one valve. The actual valves used in the apparatus are pinch valves which, when closed, clamp tubing shut to prevent fluid flow therein. The valves are also known as tubing occluding valves. Only one valve in a valve means, however, needs to be closed to constitute a closed valve means and to prevent fluid flow through a defined fluid flow path. Conversely, both named valves in a valve means must be open to constitute an open valve means. During operation of the apparatus in performing peritoneal dialysis, certain relationships among the valve means hold true.

In a basic embodiment of this invention, final fill dialysate container 30, conduit 34 and valve 38 may be omitted from dialysate supply station 10. The fifth fluid flow path and fifth valve means may also be absent, as well as fourth fluid flow path and fourth valve means. Sequencing of the valve means in the embodiment is as follows. During the heater and weigh station fill phase, first valve means (comprised of open valves 36 and 40) is open and pump 20 is pumping to allow fluid flow in the first fluid flow path (comprised of conduits 35, 18 and 22). Second valve means (comprised of open valves 40 and 42) is closed preventing fluid flow in the second fluid flow path (comprised of conduits 22 and 24). Simultaneously, the third valve means (comprised of open valves 42 and 44) is closed to prevent fluid flow in the third fluid flow path (comprised of conduits 24 and 26).

The control means in the embodiment also dictates the time interval during which the second valve means (valves 40 and 42) is open to allow fluid flow in the second fluid flow path (conduits 22 and 24) while the first valve means (valves 36 and 40) and the third valve means (valves 42 and 44) are closed and the pump is not pumping, to prevent fluid flow in the first fluid flow path and in the third fluid flow path. This phase of the cycle is the patient fill phase.

The control means further dictates which valve means are open and which valve means are closed in the patient drain phase of the basic embodiment. The third valve means (valves 42 and 44) is open to allow fluid flow in the third fluid flow path (conduits 24 and 26) while the first valve means (valves 36 and 40) and the second valve means (valves 40 and 42) are closed and the pump is not pumping to prevent fluid flow in the first fluid flow path (conduits 35, 18 and 22) and in the second fluid flow path (conduits 22 and 24).

The cycling of phases of a preferred embodiment of the peritoneal apparatus for a CCPD treatment is illustrated in the chart of FIG. 2. The cycling follows a prescribed treatment sequence for the patient. It is presumed, of course, that in operation of the apparatus, the tubing or conduit set has been primed by connecting the set to a dialysate container bag 46 (FIG. 1) at the heater and weigh station and the dialysate container bags comprising the dialysate supply station, and thereafter filling the set with dialysate.

Once the cycling has started and the tubing set has been primed, the control means controls the heating of the dialysate at the heater and weigh station. First, second and third valve means are closed and the pump means is not pumping during this initial heating. This preferred embodiment additionally comprises fourth valve means (valves 40 and 44), fifth valve means (valves 38 and 40), fourth fluid flow path (conduits 22 and 26), and fifth fluid flow path (conduits 34, 18 and 22) previously described. The fourth and fifth valve means are also closed. No dialysate is flowing through the apparatus during the initial heating.

After the dialysate has been heated to approximately body temperature (between 32° C. and 40° C.), the dialysate currently dwelling in the patient is drained to begin CYCLE I. The third valve means is opened while the first, second, fourth and fifth valve means are closed. This corresponds to open valves 42 and 44 and closed valves 40, 36 and 38. It is re-emphasized that only one valve in a valve means needs to be closed to constitute a closed valve means. All valves in a valve means must be open to constitute an open valve means. After the drain has been completed, as prescribed by a pre-set time, the patient fill phase begins.

In the patient fill phase, the third valve means is closed and the second valve means is opened. The first, fourth and fifth valve means are closed as well. Referring to FIG. 2, this corresponds to open valves 40 and 42, and closed valves 44, 36 and 38. Once the patient has been filled with dialysate, as determined by control means, the patient dwell phase begins. The first, second, third, fourth and fifth valve means are closed. Dialysate container 46 (FIG. 1) at the heater and weigh station is refilled in the next phase, although dialysate is still dwelling in the patient. During the refill of the heater and weigh station the second, third, fourth and fifth valve means are closed. This corresponds to closed valves 42, 44 and 38. First valve means is opened, corresponding to open valves 40 and 36 and a running pump 20. After the dialysate container at the heater and weigh station is filled, the first, second, third, fourth and fifth valve means are closed. The dialysate in the dialysate supply station is heated while the dialysate continues to dwell in the patient's peritoneal cavity.

In a typical CCPD treatment, CYCLE II has phases identical to CYCLE I. Any number of additional intermediate cycles identical to CYCLE II can be programmed into the control means as long as there is sufficient dialysis solution in the dialysate supply station to accommodate the cycles. A typical IPD treatment would have a greater number of intermediate cycles, and it would have a greater volume of dialysate stored in the dialysate supply station.

The final cycles in a CCPD treatment are represented as CYCLES III, IV and V in FIG. 2. CYCLE III begins with a draining of dialysate from the patient. The third valve means is open while the first, second, fourth and fifth valve means are closed. This corresponds to open valves 42 and 44 and closed valves 40, 36 and 38. After the drain has been completed, as prescribed by a pre-set time, the patient fill phase begins.

In the patient fill phase of CYCLE III, the third valve means is closed and the second valve means is opened. The first, fourth and fifth valve means are closed as well. This corresponds to open valves 40 and 42, and closed valves 44, 36 and 38. Once the patient has been filled with dialysate, the patient dwell phase begins. The first, second, third, fourth and fifth valve means are closed.

Dialysate container 46 (FIG. 1) at the heater and weigh station is drained to begin CYCLE IV. Any dialysate remaining in the heater and weigh station must be drained before final fill CYCLE V commences, using a dialysate concentration different from the preceding cycles. During the draining of the heater and weigh station, the fourth valve means is open and the first, second, third and fifth valve means are closed. This corresponds to open valves 40 and 44 and closed valves 42, 36 and 38. After the heater and weigh station has been drained, as determined by the control means, it is refilled. In this phase, the fifth valve means is open and the first, second, third and fourth valve means are closed. Pump 20 is running. This corresponds to open valves 40 and 38 and closed valves 42, 44 and 36. After the dialysate container at the heater and weigh station is filled, the first, second, third, fourth and fifth valve means are closed. The dialysate in the dialysate supply station is heated while dialysate is dwelling in the patient.

After a dwell period, the patient drain phase commences CYCLE V. The third valve means is open while the first, second, fourth and fifth valve means are closed. This corresponds to open valves 42 and 44 and closed valves 40, 36 and 38. After the drain has been completed, the patient fill phase begins. The third valve means is closed and the second valve means is opened. The first, fourth and fifth valve means are closed as well. This corresponds to open valves 40 and 42 and closed valves 44, 36 and 38.

The end of CYCLE V also ends the CCPD treatment. The connection between the patient and the apparatus at solution delivery means 14 (FIG. 1) is broken. This leaves a quantity of dialysate in the patient until that patient undergoes another CCPD treatment. Generally, the dialysate dwelling in the patient between dialysis treatments is a formulation different from the dialysate infused and drained in the earlier cycles. This dialysate is chosen especially because it will dwell in the patient for a longer period of time, that is, the time between treatments.

Figure 3:
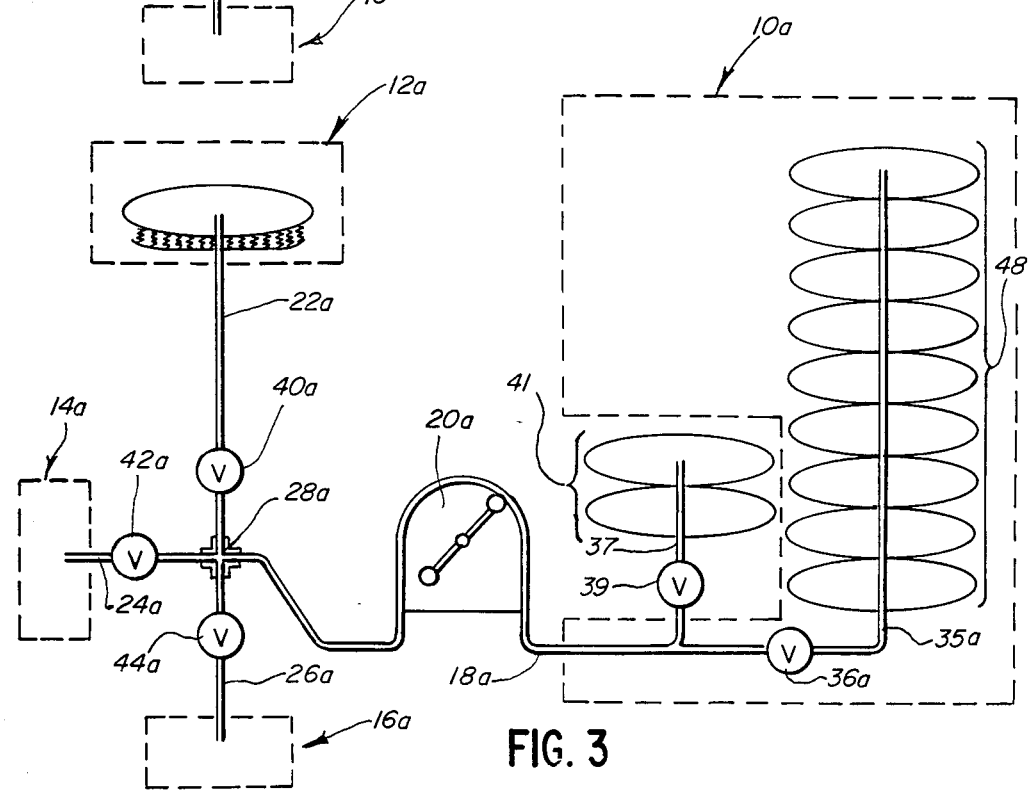
FIG. 3 is a schematic diagram showing the basic components of a peritoneal dialysis apparatus of this invention used in an IPD treatment.

FIG. 3 is a schematic representation of the basic elements in the peritoneal dialysis apparatus of the present invention when used for performing an IPD treatment. The apparatus has dialysate supply station 10a, heater and weigh station 12a, solution delivery means 14a and drain and weigh station 16a. Conduit 18a communicates with dialysate supply station 10a and passes through pump means 20a. Conduit 22a communicates with heater and weigh station 12a, conduit 24a communicates with solution delivery means 14a, and conduit 26a communicates with drain and weigh station 16a. Conduits 18a, 22a, 24a and 26a are joined together at "X" connector 28a. Valve 36a is located between conduits 18a and 35a. Valve 39 is located between conduits 18a and 37. Valves 40a, 42a and 44a regulate fluid flow in conduits 22a, 24a and 26a.

In the IPD embodiment illustrated in FIG. 3, dialysate supply station 10a is comprised of dialysate supply containers 48. Necessarily, the volume of dialysate and the number of dialysate supply containers used with the peritoneal dialysis apparatus of this invention when performing an IPD treatment would be greater than when the apparatus is performing a CCPD treatment. The embodiment of FIG. 3 optionally has conduit 37 connected to conduit 18a, valve 39 and containers 41.

Cycling in an IPD treatment would be similar to the typical CCPD cycling with two exceptions. First, more intermediate cycles with the phases of CYCLE II would be used. Second, the final cycle for IPD would terminate with a patient drain phase.

Referring back to FIG. 1 and the CCPD schematic, a sixth fluid flow path communicating with the drain and weigh station and the dialysate supply station and comprised of conduits 26, 18 and 35 additionally may be provided. Open valves 44 and 36 constitute the sixth valve means. In this alternative embodiment, spent dialysate which has been drained from the patient may be pumped from drain and weigh station 16 to dialysate supply station 10. Dialysate containers 10 would be filled with the spent dialysate. After a peritoneal dialysis procedure has been completed, dialysate containers 32 then could be disposed of conveniently.

Control means of the apparatus would close valves 42, 40 and 38 thus preventing dialysate flow through first through fifth flow paths. Control means would reverse the direction of pump means 20 to pump the spent dialysate. Sequencing of dialysate flow through sixth fluid flow path would be programmed into the control means. Referring to FIG. 3, an analogous sixth fluid flow path comprised of conduits 26a, 18a and 35a may be provided for IPD. Sixth valve means would then comprise open valves 36a, 44a and closed valves 40a, 42a and 39.

Another embodiment of the present invention would be similar to the CCPD and IPD embodiments shown in FIGS. 1 and 3 except as follows. Drain and weigh stations 16 and 16a would have an additional conduit communicating with a drain. This conduit would comprise the seventh fluid flow path. A valve located along seventh fluid flow path would constitute the seventh valve means. The control means of the apparatus would dictate the sequencing of the time intervals during which the seventh valve means would be open allowing fluid flow in the seventh fluid flow path. Drain and weigh stations 16 and 16a could then be conveniently drained whenever the volume of spent dialysate contained therein became inconvenient or difficult to dispose of.

Referring again to FIG. 3, another embodiment of an IPD apparatus would additionally comprise valve 39, conduit 37 and containers 41. Conduit 37 when connected to conduit 18a comprises the eighth fluid flow path. Open valves 44a and 39 constitute the eighth valve means. In this embodiment, spent dialysate, which has been drained from the patient, may be pumped from drain and weigh station 16a to containers 41. Control means of the apparatus would close valves 42a, 40a and 36a leaving valves 44a and 39 open, thus preventing dialysate flow through all fluid flow paths except the eighth fluid flow path defined by conduits 26a, 18a and 37.

Control means would reverse the direction of pump means 20 to pump spent dialysate to containers 41. Sequencing of dialysate flow through eighth fluid flow path would be programmed into the control means.

Figure 7:
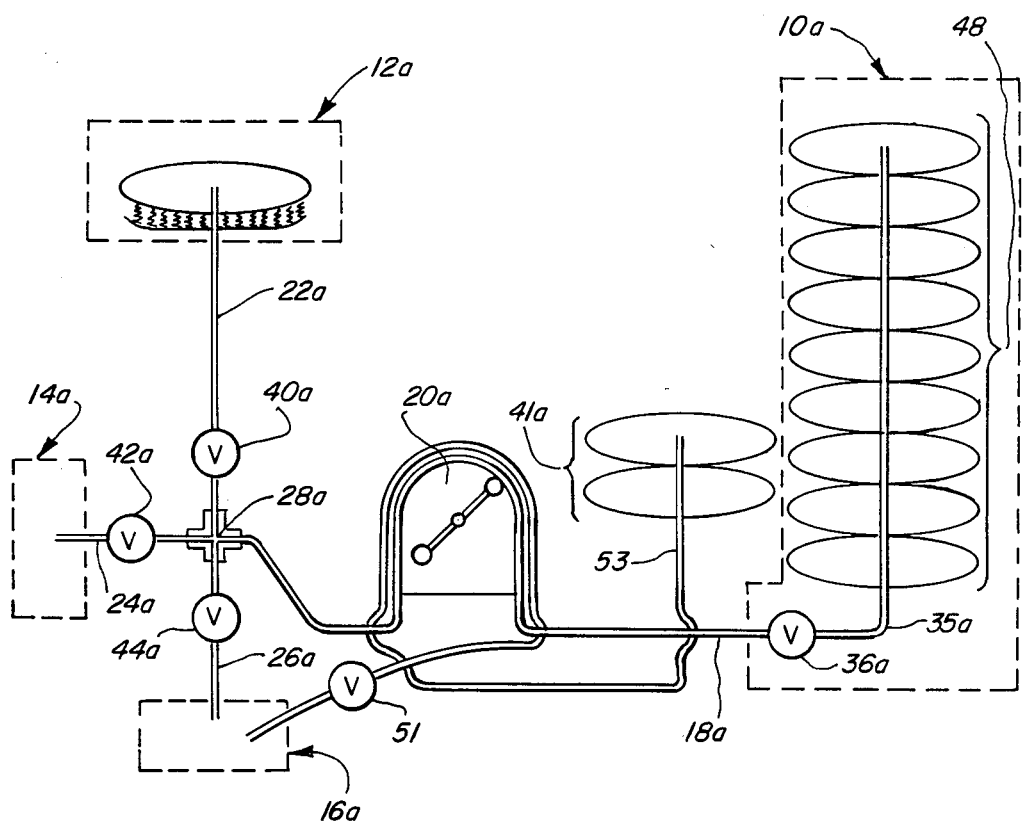
FIG. 7 is a schematic diagram showing an alternative embodiment of the peritoneal dialysis apparatus of this invention used in an IPD treatment.

Still another embodiment of an IPD apparatus is shown in FIG. 7, substantially the same as the embodiment of FIG. 3 except as noted. Valve 51 controls fluid flow in conduit 53 which defines a ninth fluid flow path. Both conduit 53 and conduit 18a pass through pump means 20a. Control means of the apparatus would sequence pumping of spent dialysate from drain and weigh station 16a to containers 41a. An advantage of this embodiment is that the action of pump means 20a is not reversed. Sequencing of dialysate flow through conduit 53, and the opening of valve 51, would be programmed into the control means.

Figure 4:
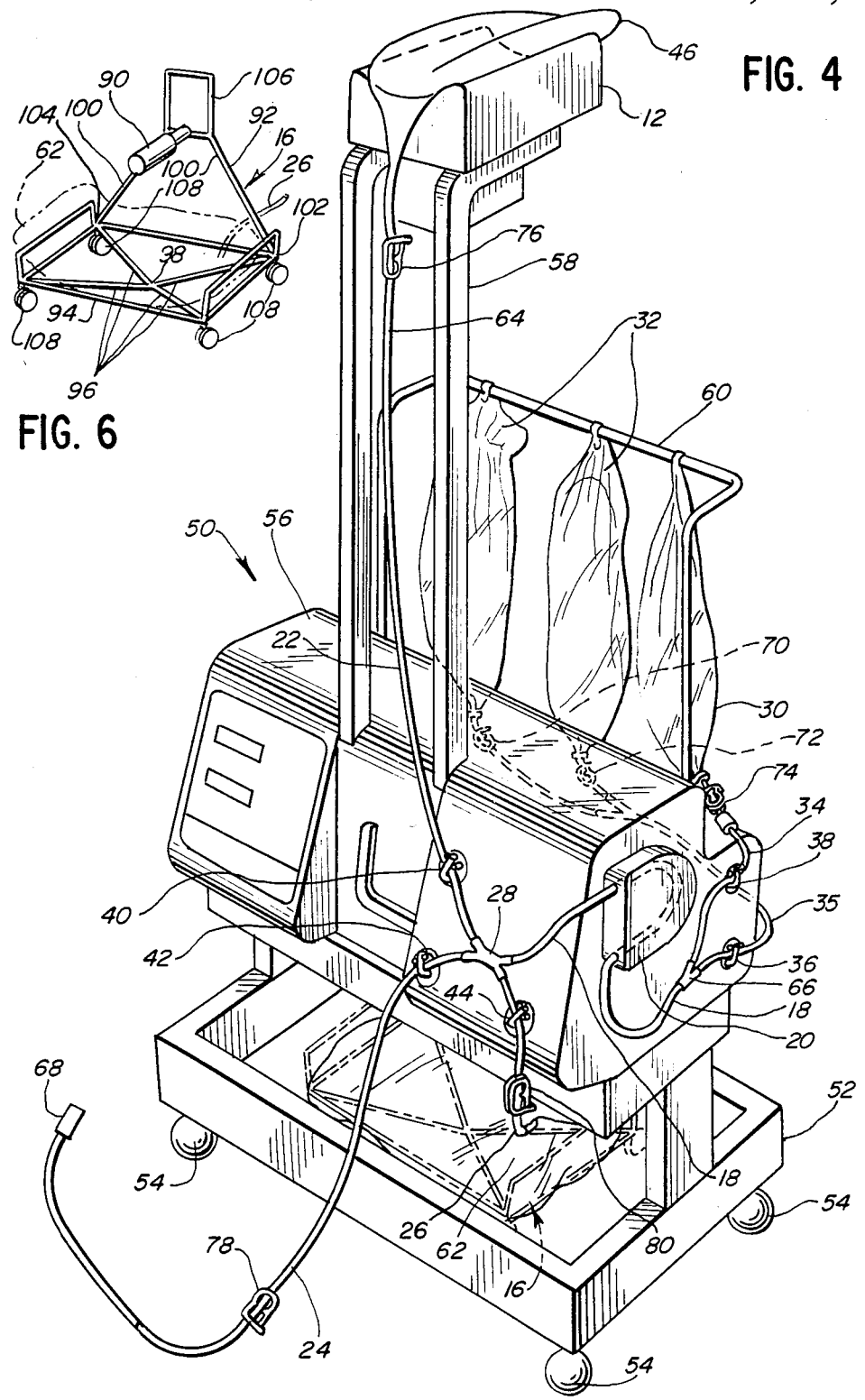
FIG. 4 is a perspective view of the peritoneal dialysis apparatus of this invention including a disposable tubing set for a CCPD treatment and dialysate container bags.

A perspective view of the peritoneal dialysis apparatus of this invention is illustrated in FIG. 4. Peritoneal dialysis apparatus 50 illustrates the basic components shown in the schematic diagram of FIG. 1. Peritoneal dialysis apparatus 50 is conveniently supported on base 52. Casters 54 attached to base 52 allow the apparatus to be moved easily. The control means of the apparatus are contained in housing 56. Support column 58 supports heater and weigh station 12. Solution bag hanger 60 is attached to the back of housing 56.

Dialysate solution container 46 rests on heater and weigh station 12, and standard dialysate containers 32 and final fill dialysate container 30 hang from hanger 60. Drain container 62 is located at the drain and weigh station.

Tubing set 64, used in CCPD treatments, communicates with the various stations of the apparatus. Conduit or tube 18 communicates with dialysate containers 30 and 32 constituting the dialysate supply station. Tube or conduit 34 connects directly to final fill dialysate container 30 and conduit 35 connects directly to standard dialysate containers 32. Conduits 34 and 35 merge with tube 18 at "Y" connection 66. Tube 18 passes through pump 20.

Tube 22 is connected to dialysate container 46, located at heater and weigh station 12. Tube 24 terminates at connector 68. Connector 68 attaches to a catheter implanted in a patient's peritoneal cavity. Tube 26 is connected to drain container 62 at the drain and weigh station. Tubes 18, 22, 24 and 26 are connected at "X" connector 28. Pinch clamps 70, 72, 74, 76, 78 and 80 are provided with tubing set 64. The pinch clamps are manually operated and are normally in their open position when the peritoneal dialysis apparatus is operating. The pinch clamps are used in the initial priming of the tubing set.

Valves 36, 38, 40, 42 and 44 are also shown on the apparatus. The valves in the apparatus are of a pinch or tubing occluding valve design. The pinch valve comprises a motor driving a gear mechanism, a link and clevis, and a spring-rod system. The valve clamp is normally in a closed-shut position with the clamp compressing the tubing therein and occluding the lumen. A spring in the pinch valve assembly, having a constant spring force, retains the clamp in its closed position. When the drive of the pinch valve is activated, the clevis therein compresses the spring and gradually opens the tubing lumen. Control of the opening and closing of the valves is dictated by the apparatus control means.

Pump 20, illustrated in FIG. 4, is a peristaltic pump of conventional design. Renal Systems, Inc., of Minneapolis, Minn. manufactures a blood pump (the RS-7850A) which is suitable for use in the apparatus of the present invention. The pump operates by external peristaltic action on the tubing of the tubing set without direct contact between the rollers of the pump and the fluid therein.

Heater and weigh station 12 is comprised of a heater plate and a weigh scale. The heater plate is bonded to a curved platen. The heater is a silicone rubber-coated heater plate which is conventionally available and known in the industry. The platen and heater plate are mounted upon a weight measuring load cell. The load cell is a commercially available product, manufactured by Hottinger Baldwin Measurements, Inc. and commonly known as a Precision Load Cell, type BBA. This single point load cell is not affected by off-center loading or residual moments. The curved platen to which the heater plate is mounted is adapted to cradle a VIAFLEX ® plastic container (VIAFLEX is a registered trademark of Baxter Travenol Laboratories, Inc.). Two thermisters, manufactured by Fenwal Electronics Co., are located on the platen to measure the temperature of the dialysate in a container at the heater and weigh station.

Prior to this invention, conventional design dialysate container bag 46 at heater and weigh station 12 would be located at a dialysate supply station. An extra container, specially designed for use as a heater bag, would be located at the heater and weigh station and affixed to and a part of the tubing set. No extra heater bag is needed in this invention. The additional heater bag is eliminated by using any conventional design dialysate container at heater and weigh station 12. The conventional design container has any desired dialysate formulation contained therein. Typically, a formulation would be the standard formulation dialysate contained in dialysate containers 32.

Support column 58, supporting the heater and weigh station, consists of two fixed length shafts. In an alternative embodiment support column 58 may be raised or lowered relative to housing 56. A spring clamp and friction pad assembly would allow the height of the support column to be easily and quickly adjusted to produce the desired head pressure for dialysate in container 46.

The drain and weigh station, illustrated in FIG. 6, is designed to accept a drain container such as container 62 shown in FIG. 4. The drain and weigh station comprises a load cell (commercially available through Hottinger Baldwin Measurements, Inc. as Precision Load Cell type BBS4). Mounted to the load cell is a freely hanging basket designed to keep the center of the basket directly under a hook on the load cell. The control means attached to the load cell measures differential weight changes and total weight of the contents of the hanging container.

Referring to FIG. 6, drain and weigh station 16 is shown. Load cell 90 is attached to the bottom portion of housing 56 (FIG. 4). Load cell 90 is also connected to the control means of the apparatus which computes differential weight measurements and total weight measurements of spent dialysate within tolerances required for CCPD and IPD including ultrafiltrate calculations. Drain and weigh station 16 further comprises basket 92 which may be formed of metal wire, plastic or other suitable materials. Basket 92 may be conveniently hung on load cell 90 for easy attachment and removal.

Basket 92 has bottom portion 94 of generally rectangular shape with structural members 96 extending from the corners of rectangular bottom portion 94 and intersecting at the center of the rectangular form in a plane below the plane of bottom portion 94 to define low point 98. Low point 98 assists in fixing the center of gravity of basket 92 in the center of the structure. Drain container 62, shown in phantom, rests in bottom portion 94 of basket 92. Tube or conduit 26 is shown connected to drain container 62.

Support hangers 100 angle from corners 102, 104 of bottom portion 94 toward a line perpendicular to the plane of bottom portion 64, passing through low point 98 but above bottom portion 94. Handle 106 may be provided at the intersection of members 100 to make handling of the basket easier. Casters 108 are located on the bottom of the basket. Casters 108 do not rest on any surface when the basket 92 is hanging from load cell 90. Casters 108 are merely provided for easy handling of a basket loaded with a filled drain bag when the dialysate contained therein is being disposed of at a disposal site away from the apparatus.

Figure 5:
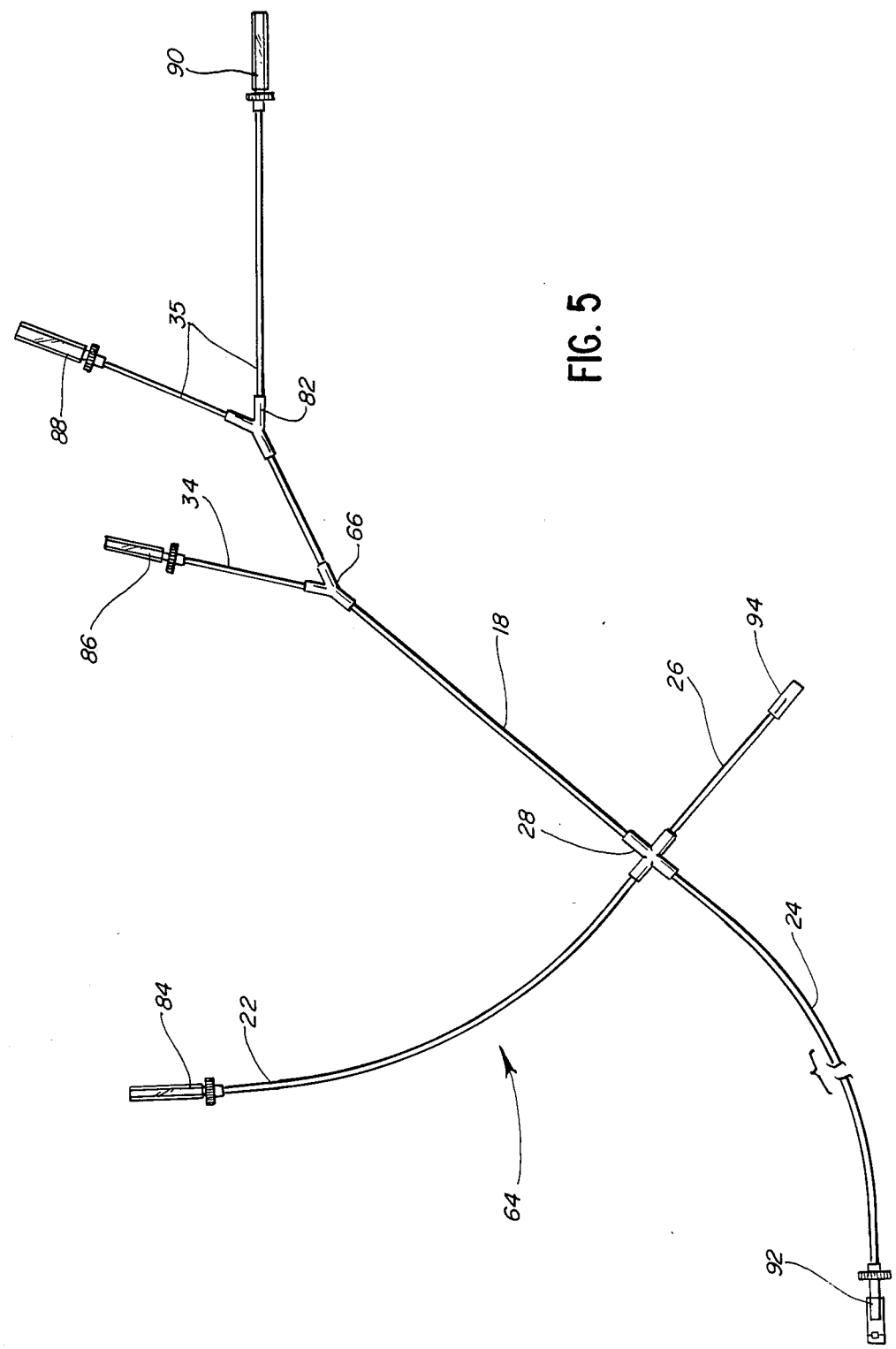
FIG. 5 is a plan view of the disposable tubing set used in the apparatus of the present invention for performing a CCPD treatment.

FIG. 5 illustrates the tubing set used with the apparatus of the present invention. Tubing set 64 comprises conduit or tube 18 for communication with the dialysate supply station of the apparatus. In a preferred embodiment of the present invention for use in CCPD therapy, additional conduits or tubes are connected to tube 18. Tube 34 is connected to tube 18 at "Y" connector 66. The "Y" connector 82 joins the two branches of tube 35 to tube 18. Tubes 34 and 35 may terminate in spikes of known design for connection to a final fill dialysate container and standard dialysate containers.

Tubes 22, 24 and 26 complete the tubes of set 64. Tubes 18, 22, 24 and 26 are interconnected at "X" connector 28. Tube 22 terminates in spike 84 for accessing a supply of heated dialysate which may be in a dialysate container. Spike 84 is of the same design as spikes 86, 88 and 90.

Tube 24 terminates in connector 92 which secures tube 24 to a peritoneal catheter implanted in a patient. Tube 26 terminates in connection device 94 for connection to a drain container in the apparatus.

The above has been offered for illustrative purposes, and is not intended to limit the invention of this application, which is defined in the claims below.

What is claimed is:

1. In a peritoneal dialysis apparatus having a dialyzate supply station, a heater and measuring station, solution delivery means, a drain and measuring station, a first fluid flow path communicating with said dialyzate supply station and said heater and measuring station, a second fluid flow path communicating with said heater and measuring station and said solution delivery means, a third fluid flow path communicating with said solution delivery means and said drain and measuring station, the improvement comprising:

means for pumping dialyzate through said first flow path;

first valve means comprising independently operable first and second tubing occluding means for controlling fluid flow in said first fluid flow path;

second valve means comprising said second tubing occluding means and a third independently operable tubing occluding means for controlling fluid flow in said second fluid flow path;

third valve means comprising said third tubing occluding means and an independently operable fourth tubing occluding means for controlling fluid flow in said third fluid flow path; and, control means including said valve means for dictating the time intervals during which:

said first and second tubing occluding means are opened to open said first valve means and said pump means is pumping to allow fluid flow in said first fluid flow path while said third and fourth tubing occluding means are closed to close said second valve means and said third valve means to prevent fluid flow in said second fluid flow path and in said third fluid flow path;

said second and third tubing occluding means are opened to open said second valve means to allow fluid flow by gravity in said second fluid flow path while said first and fourth tubing occluding means are closed to close said first valve means and said third valve means and said pump means is not pumping, to prevent fluid flow in said first fluid flow path and in said third fluid flow path; and said third and fourth tubing occluding means are opened to open said third valve means to allow fluid flow by gravity in said third fluid low path while said first and second tubing occluding means are closed to close said first valve means and said second valve means and said pump means is not pumping, to prevent fluid flow in said first fluid flow path and in said second fluid flow path.

2. The peritoneal dialysis apparatus of claim 1 and further comprising:

a fourth fluid flow path communicating between said heater and weigh station and said drain and measuring station;

fourth valve means comprising said second and fourth occluding means for controlling fluid flow in said fourth fluid flow path; and, wherein said control means selectively maintains said second tubing occluding means closed when said fourth tubing occluding means is open, and vice versa, to close said fourth valve means to prevent fluid flow in said fourth fluid flow path during the time intervals when another of said first, second, and third valve means is open, said control means further dictating the time interval during which both said second and fourth tubing occluding means are opened to open said fourth valve means to allow fluid flow in said fourth fluid flow path while said first and third tubing occluding means are closed to close said first, second, and third valve means preventing fluid flow in said first, second, and third fluid flow paths.

3. The peritoneal dialysis apparatus of claim 2 further comprising:

a sixth fluid flow path communicating with said drain and station and said dialyzate supply station;

sixth valve means comprising said first and fourth tubing occluding means for controlling fluid flow in said sixth fluid flow path; and, wherein said control means selectively maintains said first tubing occluding means closed when said fourth tubing occluding means is opened, and vice versa, to close said sixth valve means prevent fluid flow in said sixth fluid flow path during the time intervals when another of said first, second third, and fourth valve means is open, said control means further dictating the time interval during which said first and fourth tubing occluding means are both opened to open said sixth valve means and said pump means is pumping to allow fluid flow in said sixth fluid flow path while said second and third tubing occluding means are closed to close said first valve means, said second valve means, said third valve means, and said fourth valve means to prevent fluid flow in said first fluid flow path, said second fluid flow path, said third fluid flow path and said fourth fluid flow path.

4. The peritoneal dialysis apparatus of claim 1 wherein said dialyzate supply station comprises a standard dialysis solution container and a final fill dialysis solution container, wherein said first fluid flow path communicates with said standard dialysis solution container and said heater and measuring station, said apparatus further comprising:

a fifth fluid flow path communicating with said final fill dialysis solution container and said heater and measuring station, fifth valve means comprising said second tubing occluding means and an independently operable fifth tubing occluding means for controlling fluid flow in said fifth fluid flow path, and wherein during the time intervals dictated by said control means in which when said second tubing occluding means is open, said fifth tubing occluding means is closed to close said fifth valve means, and said control means further dictating the time intervals in which said second and fifth tubing occluding means are both opened to open said fifth valve means to allow fluid flow in said fifth fluid flow path while said first tubing occluding means is closed to close said first valve means to prevent fluid flow in said first fluid flow path with said third and fourth tubing occluding means closed to close said second and third valve means to prevent fluid flow in said second and third flow paths.

5. The peritoneal dialysis apparatus of claim 1 wherein "X" connector means joins together the conduits of the first, second and third flow paths to form a four-way connection to reduce tubing set length.

6. In a peritoneal dialysis apparatus having a dialyzate supply station, a heater and measuring station, solution delivery means, a drain and measuring station, a first fluid flow path communicating with said dialyzate supply station and said heater and measuring station, a second fluid flow path communicating with said heater and measuring station and said solution delivery means, a third fluid flow path communicating with said solution delivery means and said drain and measuring station, the improvement comprising:

means for pumping dialyzate;

first valve means comprising at least two separately positioned tubing occluding means for controlling fluid flow in said first fluid flow path;

second valve means comprising at least two separately positioned tubing occluding means, one of which is common to said first valve means, for controlling fluid flow in said second fluid flow path; and, third valve means comprising at least two separately positioned tubing occluding means, one of which is common to said second valve means, for controlling fluid flow in said third fluid flow path.

7. In a peritoneal dialysis apparatus having a dialyzate supply station, a dialyzate heater station, solution delivery means, and a drain and measuring station, an improved flow communication system comprising: a multiple conduit junction connection, a first conduit communicating between said junction connection and the heater station, a second conduit communicating between the junction connection and said dialyzate supply station a third conduit communicating between said junction connection and the drain and measuring station, a fourth conduit communicating between said junction connection and solution delivery means for communication with a patient, pump means for propelling dialyzate at least from said dialyzate supply station to the heater station through the second and first conduits, and valve means for controlling flow through each of said conduits.

8. The peritoneal dialysis apparatus of claim 7 in which said valve means are controlled by timer means to provide a series of operating cycles: a first operating cycle permitting flow from the dialyzate supply station to the heater station; a second operating cycle permitting flow from the heater station to the solution delivery means; and a third operating cycle permitting flow from the solution delivery means to the drain and measuring station.

9. The peritoneal dialysis apparatus of claim 7 in which said dialyzate supply station comprises at least one standard dialysis solution container and a final fill dialysis solution container, said second conduit communicating with the standard dialysis solution container, a fifth conduit, communicating between the second conduit and the final fill dialysis solution container, and added valve means controlling flow between the final fill dialysis solution container and the second conduit, whereby said added valve means can be opened to permit flow between the final fill dialysis solution container and the heater station in a final first operating cycle.

10. The peritoneal dialysis apparatus of claim 9 in which said heater station is positioned vertically higher than said solution delivery means, a solution container being positioned at said heater station which is initially separate from said first conduit and attachable thereto.

11. The peritoneal dialysis apparatus of claim 10 wherein said stations receive a disposable dialysis tubing set in which at least one container is carried at each station with flexible tubing interconnecting said containers and defining said first through fifth conduits.

12. The peritoneal dialysis apparatus of claim 9 wherein said valve means are comprised of a plurality of separately positioned tubing occluding means, with the positioning being such as to reduce tubing set length when compared to tubing set length in corresponding peritoneal dialysis apparatus having ganged valve means.

* * * * *